(12) United States Patent
Maesaka

(10) Patent No.: US 6,458,549 B2
(45) Date of Patent: *Oct. 1, 2002

(54) METHODS OF DIAGNOSING RENAL SALT WASTING SYNDROME AND ALZHEIMER'S DISEASE AND METHODS OF TREATING THE SAME

(75) Inventor: John K. Maesaka, New York, NY (US)

(73) Assignee: Winthrop-University Hospital, Mineola, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,335

(22) Filed: Jun. 11, 1998

(51) Int. Cl.$^7$ ............................................. G01N 33/567
(52) U.S. Cl. ....................... 435/7.21; 435/7.4; 435/7.92; 436/501; 436/811
(58) Field of Search ................................. 530/300, 350, 530/387.1; 435/183, 7.1, 7.21, 7.4, 7.92; 424/130.1, 178.1, 94.1, 184; 204/450; 436/500, 811, 501

(56) References Cited

PUBLICATIONS

McKhann et al., Neurology 34:939, Jul. 1984.*
Morris et al., Neurology 39:1159, Sep. 1989.*
Melegos et al, Clin Chem., 42(12)1984–91, 1996.*
Harlow and Lane, Antibodies, Cold Spring Harbor Labs, 1988.*
Andreasen et al, Arch. Neurol., V.56, 673–80, Jul. 1999.*
Y.K. Abdel–Al et al., "Bartter's Syndrome in Arabic Children: Review of 13 Cases," Pediatrics International, 41:299–303 (1999).
W.F. Falls, Jr., "Does Indomethacine Have Therapeutic Value in Salt–Wasting Renal Disease?" Virginia Medical, 105:61–62 (Jan. 1978).
J.K. Maesaka et al., "Regulation of Renal Urate Excretion: A Critical Review," Am. J. Kidney Diseases, 32(6):917–932 (Dec. 1998).
J.K. Maesaka et al., "Hypouricemia, Abnormal Renal Tubular Urate Transport, and Plasma Natriuretic Factor(s) in Patients with Alzheimer's Disease", J. Am. Ger. Soc. 41:501–506 (1993).
J.K. Maesaka et al., "Plasma Natriuretic Factor(s) in Patients with Intracranial Disease, Renal Salt Wasting and Hyperuricosuria", Life Sci. 52:1875–1882 (1993).
J.K. Maesaka et al., "Apoptosis (AP) Induced in LLC–PK1 Cells by Plasma Protein (S) in Alzheimer's Disease", J. Am. Soc. Nephrol. 6:740, Abstract (1995).
J.K. Maesaka, "Editorial: An Expanded View of SIADH, Hyponatremia and Hypouricemia", Clin. Neph. 46(2):79–83 (1996).
J.K. Maesaka et al., "Paraneoplastic Syndromes of the Kidney", Seminars in Oncology 24(3):373–381 (1997).
D.N. Melegos et al., "Prostglandin D Synthase Concentration in Cerebrospinal Fluid and Serum of Patients with Neurological Disorders", Prostaglandins 54(1):463–474 (1997).
A. Nagata et al., "Human Brain Prostaglandin D Synthase has been Evolutionarily Differentiated from Lipophilic–Ligand Carrier Proteins", Proc. Natl. Acad. Sci. USA 88:4020–4024 (1991).
E. Pennisi, "Building a Better Aspirin: New Aspirin–Like Compounds Target a Single Enzyme to Deliver Pain Relief Without Stomach and Kidney Damage. They May Also Slow the Development of Cancer and Alzheimer's Disease", Science 280:1191–1192 (1998).
"Anti–Inflammatory Agents", A Symposium: Alzheimer's Disease/Small, Am. J. Med. 104(4A) (1998).

* cited by examiner

*Primary Examiner*—Gary L. Kunz
*Assistant Examiner*—Sharon Turner
(74) *Attorney, Agent, or Firm*—Ostrolenk, Faber, Gerb & Soffen, LLP

(57) ABSTRACT

A method is described to diagnose (1) renal salt wasting syndrome and (2) Alzheimer's disease among dementia patients by measuring a patient's level of prostaglandin $D_2$ synthase. Methods are also described to (1) treat renal salt wasting syndrome, (2) inhibit the rate of apoptosis or (3) prevent the onset of, or slow the rate of, progression of Alzheimer's disease. These methods involve inhibiting the rate of $-\Delta^{12}$prostaglandin $J_2$ synthesis or by inhibiting the activity of $-\Delta^{12}$prostaglandin $J_2$.

3 Claims, 6 Drawing Sheets

METHODS OF DIAGNOSING RENAL SALT WASTING SYNDROME AND ALZHEIMER'S DISEASE AND METHODS OF TREATING THE SAME

Throughout this application, various references are referred to within parentheses. Disclosure of the publications in their entirety are hereby incorporated by reference into this application to more fully describe the state of the art to which this invention pertains.

FIELD OF THE INVENTION

The present invention relates to a method of (1) diagnosing or assessing the likelihood that a patient is afflicted with renal salt wasting syndrome and (2) diagnosing or assessing the likelihood that a patient is afflicted with or will develop Alzheimer's disease. The present invention also relates to methods of (1) treating, preventing the onset or slowing the rate of progression of Alzheimer's disease, (2) treating or preventing onset of renal salt wasting syndrome, and (3) inhibiting apoptosis.

DESCRIPTION OF THE RELATED ART

A new medical syndrome, the renal salt wasting syndrome has been described in patients suffering from pneumonia, cancers of the lung, and brain diseases such as primary or secondary tumors, brain hemorrhage, AIDS, and Alzheimer's disease (J. K. Maesaka et al. Life Sci. 52:1875, 1993, J. K. Maesaka et al., J. Am. Ger. Soc. 41:501, 1993). Patients suffering from renal salt wasting syndrome have low serum sodium (hyponatremia) and low serum uric acid levels (hypouricemia). These patients share low serum uric acid concentrations and a renal tubular transport defect for uric acid which results in an increase in the fractional excretion of uric acid. Renal salt wasting syndrome mimics the syndrome of inappropriate secretion of antidiuretic hormone (SIADH) in many clinical parameters except that renal salt wasting syndrome has diminished total body water and sodium. Total body fluids are increased in SIADH and decreased in the renal salt wasting syndrome. Because it is extremely difficult to assess accurately the fluid status of patients that do not suffer from edema, renal salt wasting syndrome patients are frequently misdiagnosed as having SIADH.

The importance of making a differentiation between renal salt wasting syndrome and SIADH is the difference in treatment modalities. SIADH is usually treated with water restriction whereas the renal salt wasting syndrome patients require variable amounts of fluid and salt supplementation depending on the extent of their salt and water deficits. Moreover, large volumes of salt and fluid, particularly water, actually exacerbate the hyponatremia in patients with SIADH which can lead to coma and convulsions. On the other hand, fluid restrictions, a common treatment for SIADH, could worsen the clinical condition of the patient with renal salt wasting syndrome because it exacerbates their underlying depletion of body fluids.

Volume depletion and persistence of the hypouricemia and increased fractional excretion (FE) of urate by the kidneys after correction of the hyponatremia distinguish renal salt wasting syndrome from the SIADH. Since assessment of extracellular volume (ECV) which is necessary to determine volume depletion has been shown to be inaccurate in non-edematous and non-ascitic cases (H. M. Chung et al., Am. J. Med. 83:905, 1987), it was postulated that it might be possible to differentiate renal salt wasting syndrome from inappropriate secretion of antidiuretic hormone by scrutinizing urate metabolism and response of the patient to saline infusion. However, the necessary salt balance studies are believed to be less practical than the simple determination described herein.

The plausibility of a salt wasting syndrome in patients with neurosurgical or possibly active brain diseases lies in the demonstration of natriuretic -apoptotic factor(s) circulating in the plasma of patients with neurosurgical and Alzheimer's diseases by Maesaka et al. (Life Sci. 52:1875, 1993; J. Am. Ger. Soc. 41:501, 1993). There was a fourfold or greater increase in apoptosis in cultured LLC PK1 cells that have been exposed to Alzheimer plasma as compared to normal and multi-infarct dementia (MID) plasma (J. K. Maesaka et al., J. Am. Soc. Nephrol. 6:740, 1995 (abst.)). However, the identity of this factor is not known and the testing of its presence based on an increase in apoptosis in tissue cultured cells is impractical.

SUMMARY OF THE INVENTION

It is an object of the present invention to provide effective methods and kits for diagnosing Alzheimer's disease and renal salt wasting syndrome.

It is another object of the invention to provide a method of treating, reducing the risk of onset of, or slowing the rate of progression of, Alzheimer's disease.

It is yet another object of the invention to provide a method to treat or reduce onset of renal salt wasting syndrome.

It is yet another object of the invention to provide a method to inhibit the rate of apoptosis.

It is yet another object of the invention to provide a clinical kit for the quantification of prostaglandin $D_2$ synthase levels, preferably for aiding diagnosis of Alzheimer's disease and/or renal salt wasting syndrome.

In one embodiment, the invention provides a method of diagnosing or assessing the likelihood that a patient is afflicted with renal salt wasting syndrome, said method comprising measuring the level of prostaglandin $D_2$ synthase in a sample from said patient.

In another embodiment, the invention provides a method of diagnosing or assessing the likelihood that a patient is afflicted with Alzheimer's disease, said method comprising measuring the level of prostaglandin $D_2$ synthase in a sample from said patient.

In yet another embodiment, the invention provides a method of treating or reducing the risk of acquiring renal salt wasting syndrome in a patient in need of such treatment or reduction, said method comprising reducing $-\Delta^{12}$prostaglandin $J_2$ levels or activity thereof in said patient.

In yet another embodiment, the invention provides a method of inhibiting the rate of apoptosis in a patient with elevated prostaglandin $D_2$ synthase in the plasma or urine, said method comprising reducing $-\Delta^{12}$prostaglandin $J_2$ levels or activity in said patient.

In yet another embodiment, the invention provides the method of treating or reducing the risk of onset of Alzheimer's disease in a patient in need of such treatment or reduction, said method comprising reducing $-\Delta^{12}$prostaglandin $J_2$ levels, or activity thereof, in said patient, other than by administering a cyclo-oxygenase inhibitor.

In yet another embodiment, the invention provides a diagnostic kit for detecting the presence of prostaglandin $D_2$ synthase in a sample, said kit comprising antibodies to said prostaglandin $D_2$ synthase, and means for measuring prostaglandin $D_2$ synthase:anti-prostaglandin $D_2$ synthase immunocomplexes.

The term "inhibitor" as used herein means any agent which reduces the normal physiological effect of an already-formed agent, e.g. by action on the agent itself or by antagonistic effect on a receptor for that agent. EXCEPTION: As used herein, the term "cyclo-oxygenase inhibitor" does not include cyclo-oxygenase antibodies.

BRIEF DESCRIPTION OF THE DRAWINGS

FIG. 2A is a light micrograph of a TUNEL assay performed on LLC-PK1 cells exposed to control plasma for 2 hours showing normal pale staining nuclei. FIG. 2B is a light micrograph of a TUNEL assay performed on LLC-PK1 cells exposed to plasma of patients with Alzheimer's disease for 2 hours showing condensed, dark nuclei (large arrowheads) and the normal oval pale nuclei (small arrowheads). Magnification=300×. This shows that LLC-PK1 cells undergo apoptosis after exposure to AD plasma.

FIG. 6A depicts fractionation of 0.5 M NaCl eluate from Affi-Blue run on Rotofor (BioRad) using pH 3–10 gradient. FIG. 6B depicts fractionation of the active pool from FIG. 6A (pI 4.4–5.7) on Rotofor, using pH 4–6 gradient. Arrow points to fraction 2, line represents the active fraction.

DETAILED DESCRIPTION OF THE INVENTION

Figure 1:
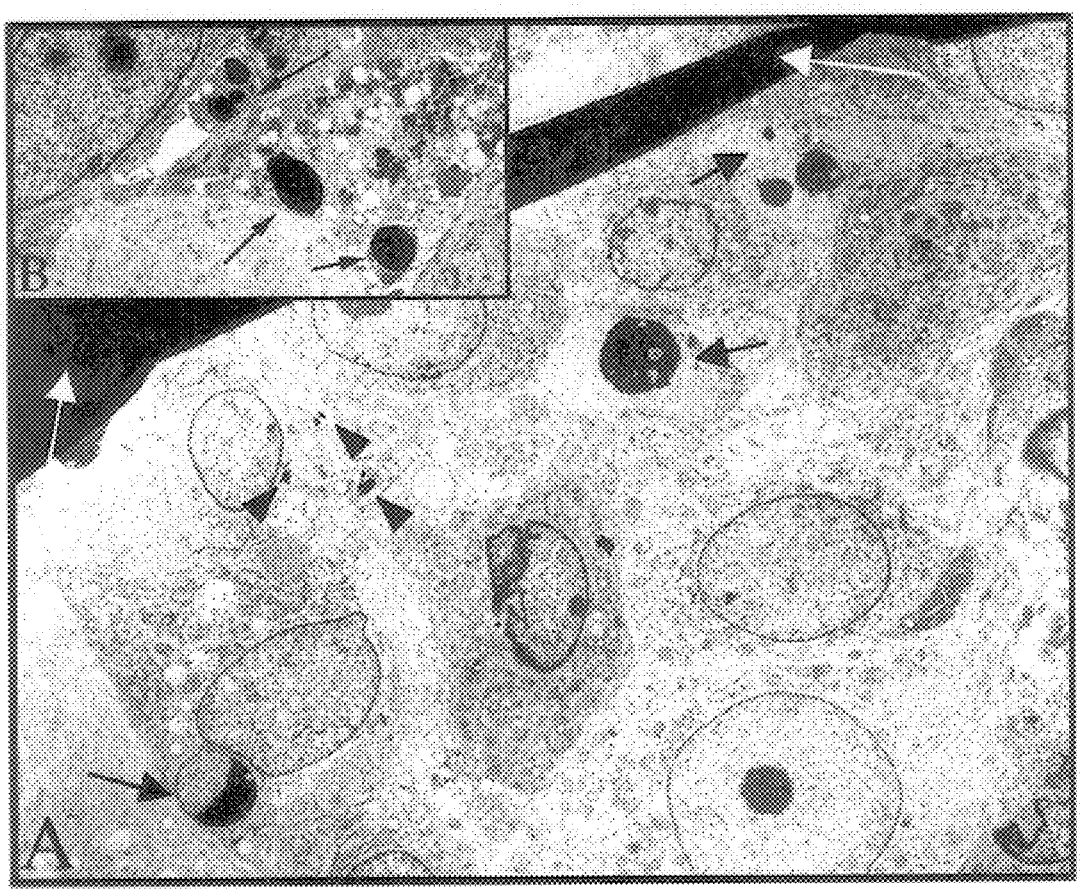
FIGS. 1A and 1B shows a transmission electron micrograph of LLC-PK1 cells that have been exposed to AD plasma for 2 hours prior to fixation. Note condensed and black nuclei (black arrows). Arrowheads represent small residual nuclear bodies engulfed by a neighboring cell. White arrows show a section fold. Magnification: A=2200×, B=4500×. This shows that LLC-PK1 cells undergo apoptosis after exposure to AD plasma.

In accordance with the invention, prostaglandin $D_2$ synthase is a marker for Alzheimer's disease and is also a marker for renal salt wasting syndrome. Levels of Prostaglandin $D_2$ synthase are elevated in the blood and urine of patients suffering from Alzheimer's disease as compared to normal, non-demented age and gender-matched controls and comparably demented patients with multi-infarct dementia.

The levels of prostaglandin $D_2$ synthase are also elevated in the blood and urine of patients suffering from renal salt wasting syndrome and not in patients with the syndrome of inappropriate secretion of antidiuretic hormone (SIADH), a common cause of hyponatremia.

The bioassay of the present invention to determine the presence of prostaglandin $D_2$ synthase provides a simple means of differentiating renal wasting syndrome from SIADH. The bioassay of the present invention also provides simple means of differentiating Alzheimer's disease from multi-infarct dementia. These clinical differentiations are often difficult to make. The importance of making a differentiation between both renal salt wasting syndrome and SIADH is the difference in treatment modalities.

Clinical differentiation between Alzheimer's disease and other dementia type of diseases such as multi-infarct dementia is also very important particularly at the earliest stages of the disease when diagnosis is very difficult. Early diagnosis of Alzheimer's disease may be particularly helpful because it might lead to early treatment before more damage is done to the brain.

Diagnosis of Alzheimer's Disease and Renal Salt Wasting Syndrome by Detecting Prostaglandin $D_2$ Synthase A sample is normally taken from a subject suspected of having renal salt wasting syndrome or Alzheimer's disease. This sample is then tested to measure the level of prostaglandin $D_2$ synthase. An elevated level of prostaglandin $D_2$ synthase over control samples (e.g. one or two standard deviations above normal, and especially levels more than twice the normal level) is an indication of renal salt wasting syndrome or of Alzheimer's disease. The method of the invention and detection kits in accordance with the invention, preferably include comparison standards derived from previously tested control samples. The method of the invention may be practiced by comparing measured levels of prostaglandin $D_2$ synthase (in a test sample) to the comparison standards. Likelihood that the patient suffers from Alzheimer's disease or renal salt wasting syndrome derived from correlation of measured levels to the comparison standards. The comparison standards may be any well known in the art, e.g. color change, phosphorescence, enzymatic activity or any other parameter common in the art. Some examples are set forth below in the section entitled "Methods of Detection of Prostaglandin $D_2$ Synthase". Naturally, the comparison standards should reflect control levels measured by the same measurement technique as will be utilized for measuring prostaglandin $D_2$ synthase in the patient sample. It is preferred that the comparison standard show any age and gender-based variations.

Preferably, the samples to be tested are body fluids such as blood, plasma, urine, tears, saliva and the like. Both medical and veterinary applications are contemplated. In addition to human samples, samples may be taken from other mammals such as non-human primates, horses, swine, etc. In some instances it may be possible or even desirable to dilute the sample prior to testing. Plasma, when used as the sample, may be diluted, for example, with one or more fluids selected from the group consisting of phosphate-buffered saline, pH 7.0–7.4 (hereinafter "PBS"), PBS-containing TWEEN 20 (hereinafter "PBS T"), PBS T with thimerosal (hereinafter "PBS TT"), PBS TT (gelatin) (hereinafter "PBS TTG").

Preferred diluents and dilution ratios may vary in a known manner according to the sample being tested. In some instances, it can be desirable to concentrate a sample that is initially too dilute. Prior to testing a sample whose pH is outside of the preferred pH for antibody function (e.g. urine), the pH of the sample is preferably adjusted to between about 7.0 and 7.4, the preferred pH for antibody function.

Prostaglandin $D_2$ Antibody Preparation (i) Polyclonal Antibodies

Polyclonal antibodies to prostaglandin $D_2$ or prostaglandin $D_2$ fragments can generally be raised in animals by multiple subcutaneous (sc), intradermal (id), or intraperitoneal (ip) injections of natural or recombinant prostaglandin $D_2$ synthase or prostaglandin $D_2$ synthase fragment or synthetic peptide and an adjuvant. It may be useful to conjugate prostaglandin $D_2$ synthase or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, or SOCl2.

Animals can be immunized against the prostaglandin $D_2$ synthase protein or a fragment thereof, immunogenic conjugates, or derivatives by combining 1 mg or 1 μg of the peptide or conjugate (for rabbits or mice, respectively) with 3 volumes of Freund's complete adjuvant or other adjuvant and injecting the solution intradermally at multiple sites. Four to five weeks later the animals are boosted with ⅕ to ⅒ the original amount of peptide or conjugate in Freund's complete adjuvant by subcutaneous injection at multiple sites or intradermal injection at multiple sites of an equivalent amount of natural or recombinant prostaglandin $D_2$ synthase. Seven to 14 days later the animals are bled and the serum is assayed for prostaglandin $D_2$ synthase or prostaglandin $D_2$ synthase fragment antibody titer. Animals are boosted until the titer plateaus. Preferably, the animal is boosted with purified natural or recombinant prostaglandin $D_2$ synthase, the conjugate of the same prostaglandin $D_2$ synthase or prostaglandin $D_2$ synthase fragment, but conjugated to a different protein and/or through a different cross-linking reagent. Conjugates also can be made in recombinant cell culture as protein fusions Also, aggregating agents such as alum may be used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the prostaglandin $D_2$ synthase monoclonal antibodies of the invention may be made using the hybridoma method (Nature, 256: 495 (1975), or may be made by known recombinant DNA methods.

In the hybridoma method, a mouse or other appropriate host animal, such as a hamster, is immunized as hereinabove described to elicit lymphocytes that produce or are capable of producing antibodies that will specifically bind to the prostaglandin D2 synthase or prostaglandin $D_2$ synthase fragment used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp.59–103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. U.S.A., and SP-2 cells available from the American Type Culture Collection, Rockville, Md. U.S.A.

Culture medium in which hybridoma cells are growing is assayed for production of monoclonal antibodies directed against prostaglandin $D_2$ synthase. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson and Pollard, Anal. Biochem., 107: 220 (1980).

After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). Once isolated, the DNA may be placed into expression vectors. Host cells are then transformed or transfected with said vectors. Suitable host cells include but are not limited to *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding an antibody include Skerra et al., Curr. Opinion in Immunol., 5: 256–262 (1993) and Pluckthun, Immunol. Revs., 130: 151–188 (1992).

The DNA also may be modified, for example, by substituting the coding sequence for human heavy- and light-chain constant domains in place of the homologous murine sequences (Morrison, et al., Proc. Nat. Acad. Sci., 81: 6851 [1984]), or by covalently joining to the immunoglobulin coding sequence all or part of the coding sequence for a non-immunoglobulin polypeptide. In that manner, "chimeric" or "hybrid" antibodies are prepared that have the binding specificity of an anti-prostaglandin $D_2$ synthase monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a prostaglandin $D_2$ synthase and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(iii) Human Antibodies

Human monoclonal antibodies can be made by the hybridoma method. Human myeloma and mouse-human heteromyeloma cell lines for the production of human monoclonal antibodies have been described, for example, by Kozbor, J. Immunol. 133, 3001 (1984); Brodeur, et al., Monoclonal Antibody Production Techniques and Applications, pp. 51–63 (Marcel Dekker, Inc., New York, 1987); and Boerner et al., J. Immunol., 147: 86–95 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (J[H]) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255–258 (1993); Bruggermann et al., Year in Immuno., 7: 33 (1993).

Alternatively, phage display technology (McCafferty et al., Nature, 348: 552–553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., Current Opinion in Structural Biology, 3: 564–571 (1993). Several sources of V-gene segments can be used for phage display. Clackson et al., Nature, 352: 624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol., 222: 581–597 (1991), or Griffith et al., EMBO J., 12: 725–734 (1993).

In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol., 10: 779–783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., Nucl. Acids Res., 21: 2265–2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT WO 93/06213, published Apr. 1, 1993). Unlike traditional humanization of rodent antibodies by CDR grafting, this technique provides completely human antibodies, which have no framework or CDR residues of rodent origin.

Methods of Detection of Prostaglandin $D_2$ Synthase

Detection with Antibodies

For diagnostic applications (i.e. detection of prostaglandin $D_2$ synthase), antibodies against prostaglandin $D_2$ synthase typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$; a fluorescent or chemiluminescent compound (Melegos et al., Clin. Chem. 42:12 (1996)), such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody to the detectable moiety may be employed, including those methods described by Hunter et al., Nature, 144: 945 (1962); David et al., Biochemistry, 13: 1014 (1974); Pain et al., J. Immunol. Meth., 40: 219 (1981); and Nygren, J. Histochem. and Cytochem., 30: 407 (1982).

The antibodies used for diagnostic purposes in the present invention may be employed in any known assay method, such as competitive binding assays, direct and indirect sandwich assays, and immunoprecipitation assays. Zola, Monoclonal Antibodies: A Manual of Techniques, pp. 147–158 (CRC Press, Inc., 1987).

Competitive binding assays rely on the ability of a labeled standard (which may be prostaglandin $D_2$ synthase or an immunologically reactive portion thereof) to compete with the test sample for binding with a limited amount of antibody. The amount of prostaglandin $D_2$ synthase in the test sample is inversely proportional to the amount of standard that becomes bound to the antibodies. To facilitate determining the amount of standard that becomes bound, the antibodies generally are insolubilized before or after the competition, so that the standard and prostaglandin $D_2$ synthase from the tested sample that are bound to the antibodies may conveniently be separated from the unbound material.

Sandwich assays involve the use of two antibodies, each capable of binding to a different immunogenic portion, or epitope, of the protein (prostaglandin $D_2$ synthase) to be detected. In a sandwich assay, the test sample protein (prostaglandin $D_2$ synthase) is bound by a first antibody which is immobilized on a solid support, and thereafter a second antibody binds to the protein, thus forming an insoluble three-part complex. David and Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay (Enzyme Linked immunoabsorbent assay), in which case the detectable moiety is an enzyme (e.g., horseradish peroxidase).

Prostaglandin $D_2$ synthase antibodies are useful in diagnostic assays for prostaglandin $D_2$ synthase, e.g., its production in specific cells or tissues, or its presence in urine or serum. The antibodies are labeled and/or are immobilized on an insoluble matrix. In one embodiment, an antibody that binds to prostaglandin $D_2$ synthase is immobilized on an insoluble matrix, the test sample is contacted with the immobilized antibody composition to adsorb all prostaglandin $D_2$ synthase, and then the immobilized prostaglandin $D_2$ synthase molecules are contacted with antibodies that recognize different antigenic sites on prostaglandin $D_2$ synthase, these antibodies being identifiable by a unique label such as discrete fluorophores or the like. By determining the presence and/or amount of the unique label, the amount of prostaglandin $D_2$ synthase can be determined.

Competitive assays rely on the ability of a tracer (i.e. labelled) analogue to compete with the test sample prostaglandin $D_2$ synthase for a limited number of binding sites on a common binding partner. The binding partner generally is insolubilized before or after the competition and then the tracer and prostaglandin $D_2$ synthase bound to the binding partner are separated from the unbound tracer and prostaglandin $D_2$ synthase. This separation is accomplished by decanting (where the binding partner was preinsolubilized) or by centrifuging (where the binding partner was precipitated after the competitive reaction). The amount of test sample prostaglandin $D_2$ synthase is inversely proportional to the amount of bound tracer as measured by the amount of marker substance. Dose-response curves with known amounts of prostaglandin $D_2$ synthase are prepared and compared with the test results to quantitatively determine the amount of prostaglandin $D_2$ synthase present in the test sample. These assays are called ELISA systems when enzymes are used as the detectable markers.

Another species of competitive assay, called a "homogeneous" assay, does not require a phase separation. Here, a conjugate of an enzyme with prostaglandin $D_2$ synthase is prepared and used such that when anti-prostaglandin $D_2$ synthase binds to the prostaglandin $D_2$ synthase, the presence of the anti-prostaglandin $D_2$ synthase modifies the enzyme activity. In this case, prostaglandin $D_2$ synthase or its immunologically active fragments are conjugated with a bifunctional organic bridge to an enzyme such as peroxidase. Conjugates are selected for use with anti-prostaglandin $D_2$ synthase so that binding of the anti-prostaglandin $D_2$ synthase inhibits or potentiates the enzyme activity of the label. This method per se is widely practiced under the name of EMIT.

Sandwich assays particularly are useful for the determination of prostaglandin $D_2$ synthase. In sequential sandwich assays an immobilized binding partner is used to adsorb test sample prostaglandin $D_2$ synthase, the test sample is removed as by washing, the bound prostaglandin $D_2$ synthase is used to adsorb labeled binding partner, and bound material is then separated from residual tracer. The amount of bound tracer is directly proportional to test sample prostaglandin $D_2$ synthase. In "simultaneous" sandwich assays the test sample is not separated before adding the labeled binding partner. A sequential sandwich assay using an anti-prostaglandin $D_2$ synthase monoclonal antibody as one antibody and a polyclonal anti-prostaglandin $D_2$ synthase antibody as the other is useful in testing samples for prostaglandin $D_2$ synthase presence.

Detection with Assay for Apoptosis

Applicant demonstrated the presence of a factor (isolated and identified as prostaglandin $D_2$ synthase) in the plasma of patients with Alzheimer's disease that increases apoptosis in cultured LLC-PK1 cells when compared to plasma from control subjects (C) and subjects suffering from multi-infarct dementia (MID). To verify this result, applicant also demonstrated (infra) that addition of $-\Delta^{12}$prostaglandin $J_2$ to cultured LLC-PK1 cells increases the rate of apoptosis.

The determination of apoptosis can be done in a variety of ways such as a TUNEL assay, demonstration of a nucleosomal ladder by agarose gel electrophoresis, and electron micrographic analysis showing typical morphology of apoptosis.

The conclusion that apoptosis results from the presence of a factor (i.e. prostaglandin $D_2$ synthase) in the plasma of patients suffering from Alzheimer's disease is based on observed DNA degradation in nuclei of affected cells. The degree of apoptosis was dose and time dependent, continually increasing up to at least 8 h with renewed sampling of Alzheimer's plasma every 2 h. The apoptotic ladder seen by agarose gel electrophoresis results from the double-stranded endonucleolytic cleavage of DNA which occurs at the linker regions of nucleosomes to produce fragments of multiples of about 180 bp. This fragmentation of DNA appears coincident with condensation of nuclear chromatin prior to cell death and is considered a characteristic biochemical feature of apoptosis (Y. Gavrieli et al., J. Cell. Biol. 119:493–501, 1992). Demonstration of this repeat pattern was, therefore, used as an indicator of apoptosis. The 3'OH ends of this cleaved DNA can also serve as substrate for deoxynucleotidyl terminal transferase TdT, which led to the development of TdT-mediated dUTP-biotin nick end labeling (TUNEL) (Y. Gavrieli et al., J. Cell. Biol. 119:493–501, 1992). This technique results in the labeling of nuclei in-situ, prior to the appearance of the ladder by gel electrophoresis. TUNEL staining of DNA fragments occurs not only in histologically-defined apoptotic cells but also in intact cells during the early stages of apoptosis (Y. Gavrieli et al., J. Cell. Biol. 119:493–501, 1992). Electron microscopy of the nuclei of LLC-PK1 cells shows chromosomal fragmentation (nuclear condensation) upon exposure to prostaglandin $D_2$ synthase.

Prostaglandin $D_2$ synthase may also be detected in an enzymatic assay according to the method described by Urade et al. (J. Bio. Chem. 270: 1422–1428; 1995).

The foregoing are merely exemplary diagnostic assays for detection of prostaglandin $D_2$ synthase in accordance with the invention. Because it is the level of prostaglandin $D_2$ synthase that is relevant, any other technique that effectively measures prostaglandin $D_2$ synthase is also included within the scope hereof.

Treatment of Alzheimer's Disease and Renal Salt Wasting Syndrome

Prostaglandin $D_2$ synthase plays a role in the synthesis pathway of $\Delta^{12}$prostaglandin $J_2$. Arachidonic acid is initially converted by cyclo-oxygenase to prostaglandin $H_2$. Prostaglandin $D_2$ synthase, is an enzyme that converts prostaglandin $H_2$ to prostaglandin $D_2$. Prostaglandin $D_2$ then spontaneously converts to $\Delta^{12}$prostaglandin $J_2$, presumably the biologically active metabolite of this pathway.

Without intending to be bound by theory, it is believed that the presence of prostaglandin $D_2$ synthase in the urine and blood of patients suffering from Alzheimer's disease or renal salt wasting syndrome is an indication of an excess of this enzyme at least in some regions of the patient's body which evidently results in excess production of $-\Delta^{12}$prostaglandin $J_2$. Along this line, more prostaglandin $H_2$ gets converted into prostaglandin $D_2$ which is spontaneously (i.e. immediately and without the need of an enzyme) converted to prostaglandin $J_2$ and then to $-\Delta^{12}$prostaglandin $J_2$.

Applicant found that prostaglandin $D_2$ synthase increased apoptosis of human kidney proximal tubule cells in culture. However, $-\Delta^{12}$prostaglandin $J_2$ was the only prostaglandin in the above pathway that induces apoptosis. $-\Delta^{12}$Prostaglandin $J_2$ increased apoptosis to the same degree as prostaglandin $D_2$ synthase. The addition of prostaglandin $D_2$ synthase and indomethacin, which inhibits cyclo-oxygenase and reduces the prostaglandin synthesis downstream did not increase apoptosis above baseline. The inhibition of prostaglandin $D_2$ synthase by N-Ethyl Maleimide inhibited apoptosis. In addition, combination of indomethacin, prostaglandin $D_2$ synthase and $-\Delta^{12}$prostadlandin $J_2$ increased apoptosis. Furthermore, addition of $-\Delta^{12}$prostadlandin $J_2$ to indomethacin increased apoptosis. All these results indicate that prostaglandin $D_2$ synthase causes apoptosis by helping to produce more of $-\Delta^{12}$prostaglandin $J_2$. Thus, the present invention seeks to reduce $-\Delta^{12}$prostaglandin $J_2$ levels.

Furthermore, it is believed that Alzheimer's disease is the result of neuronal brain cells undergoing apoptotic cell death. It is also believed that renal salt wasting syndrome might be the result of apoptotic cell death by kidney tubule cells. Therefore, inhibiting the rate of apoptosis which, at least in part, is caused by elevated $-\Delta^{12}$prostaglandin $J_2$ levels is expected to be an effective treatment for both Alzheimer's disease and renal salt wasting syndrome.

Accordingly, the present invention provides methods of (1) treating or reducing risk of onset of renal salt wasting syndrome, (2) inhibiting the rate of apoptosis, and (3) reducing the risk of onset, or treating (e.g. by slowing the rate of progression of) Alzheimer's disease. The methods inhibit the effect of, or reduce the levels of $-\Delta^{12}$prostaglandin $J_2$ levels.

Reduction of $-\Delta^{12}$prostaglandin $J_2$ Activity

The reduction of $-\Delta^{12}$prostaglandin $J_2$ levels can be accomplished in a wide variety of ways, for example those set forth below.

1) Inhibiting the rate of synthesis of $-\Delta^{12}$prostaglandin $J_2$. This can be accomplished by administering at least one agent selected from the group consisting of cyclo-oxygenase inhibitor, cyclo-oxygenase antibody, prostaglandin $D_2$ synthase inhibitor, prostaglandin $D_2$ synthase antibody. The cyclo-oxygenase inhibitor can be for example indomethacin and prostaglandin $D_2$ synthase inhibitor can be N-ethyl maleimide.

2) Increasing the rate of degradation or elimination of $-\Delta^{12}$prostaglandin $J_2$. This can be accomplished for example by adding an agent that increases the rate of catabolism or the rate of turnover of $-\Delta^{12}$prostaglandin $J_2$.

3) Administering to the subject an inhibitor of $-\Delta^{12}$prostaglandin $J_2$ (e.g. a receptor antagonist).

Pharmaceutical Administration

In accordance with one aspect of the invention, once Alzheimer's disease or renal salt wasting syndrome is diagnosed, at least one agent selected from the group of cyclo-oxygenase inhibitor, cyclo-oxygenase antibody, prostaglandin $D_2$ synthase inhibitor, prostaglandin $D_2$ synthase antibody, and $\Delta^{12}$prostaglandin $J_2$ inhibitor, is(are) administered at a dosage sufficient to reach the affected location (for example, the brain or kidney) and reduce the rate of apoptosis. Non-limiting examples of methods of administration and dosages which apply to both treatment and prevention are detailed below. Dosages will be the same when the invention is used prophylactically, preferably for patients at higher risk than the general population of acquiring the disease in question. Risk factors are known in the art. As used herein, a "patient" may be a human or other mammalian patient. Veterinary use of the inventions herein are appropriate.

As used in the invention, any of the above-identified agents may be administered with or without additional carrier or diluent by the oral, systemic, percutaneous, transmucosal, or other typical route. In a pharmaceutical composition for oral administration, an agent as described above is preferably present in a concentration between 5 and 99% by weight relative to total weight of the composition, more preferably between 50 and 99 percent, especially between 80 and 99 percent.

When prepared for percutaneous administration, an agent is preferably present in a concentration between 2 and 20% by weight relative to the total weight of the composition, more preferably between 5 and 15%, especially between 5 and 10%.

Oral Administration

When administered by the oral route, the agent described hereinabove may be formulated with conventional pharmaceutical excipients, e.g. spray dried lactose and magnesium stearate, into tablets or capsules for oral administration at concentrations providing easy dosage in a range from 1 ng to 10 g, preferably, from 1–10 mg per day per kg of body weight.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms. The active substance can be also administered in solid dispersion state in appropriate carriers. Such carriers may, for example, be chosen from the group consisting of polyethylene glycols of molecular weight varying from 1,000 to 20,000 daltons and polyvinylpyrrolidone (e.g., Povidone from American Chemicals Ltd., Montreal, Canada).

As further forms, one can use plug capsules, e.g. of hard gelatin, as well as closed soft-gelatin capsules comprising a softener or plasticizer, e.g. glycerine. The plug capsules contain the active substance preferably in the form of granulate, e.g. in mixture with fillers, such as lactose, saccharose, mannitol, starches such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

Topical Administration

For the treatment of conditions associated with apoptosis of the skin, the preferred mode of administration is topical. Any pharmaceutically acceptable base typically used in the art for preparing formulations in the form of topical gels, ointments, lotions, or the like may be used as the base. The agent described above is preferably provided at a concentration of 0.001–10%, more preferably 0.1–1% by weight of the total formulation. One to two applications per day to the affected area are recommended.

Transdermal Delivery

When the composition of the present invention is formulated as an ointment, lotion, gel, cream or the like, for transdermal administration, the active compound is admixed with a suitable carrier which is compatible with human skin or mucosa and which enhances transdermal or transmucosal penetration of the compound through the skin or mucosa. Suitable carriers are known in the art and include but are not limited to Klucel HF and Glaxal base which is available from Glaxal Canada Limited. Other suitable vehicles can be found in Koller and Buri, S.T.P. Pharma 3(2), 115–124, 1987. The carrier is preferably one in which the active ingredient(s) is(are) soluble at ambient temperature at the concentration of active ingredient that is used. The carrier should have sufficient viscosity to maintain the precursor on a localized area of skin or mucosa to which the composition has been applied, without running or evaporating for a time period sufficient to permit substantial penetration of the precursor through the localized area of skin. The carrier is typically a mixture of several components, e.g. pharmaceutically acceptable solvents and a thickening agent. A mixture of organic and inorganic solvents can aid hydrophilic and lipophilic solubility, e.g. water and an alcohol such as ethanol. Desirably, the carrier is one which, if applied twice daily in an amount providing 1 ng to 10 g, preferably 1 mg to 1 g, and more preferably 100 mg 1 g of agent to the afflicted area, will provide blood serum levels sufficient to reduce apoptosis in the effected tissues.

The carrier may include various additives commonly used in ointments, lotions, gels, and creams and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The lotion, ointment, gel or cream should be thoroughly rubbed into the skin so that no excess is plainly visible, and the skin would not be washed in that region until most of the transdermal penetration has occurred, preferably, at least 15 minutes and, more preferably, at least 30 minutes after application.

A transdermal patch may be used to deliver the composition of the present invention in accordance with known techniques. It is typically applied for a long period, e.g. 0.5 to 4 days, but typically contacts active ingredients to a smaller surface area, allowing a slow and constant delivery of active ingredient.

A number of transdermal drug delivery systems that have been developed, and are in use, are suitable for delivering the active ingredient of the present invention. The rate of release is typically controlled by a matrix diffusion, or by passage of the active ingredient through a controlling membrane.

Mechanical aspects of transdermal devices are well known in the art, and are explained, for example, in U.S. Pat. Nos. 4,162,037, 5,154,922, 5,135,480, 4,666,441, 4,624, 665, 3,742,951, 3,797,444, 4,568,343, 4,064,654, 5,071,644, 5,071,657, the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to he patient's skin. In U.S. Pat. No. 4,135,480, the disclosure of which is incorporated by reference, Bannon et al. described an alternative device having a non-adhesive means for securing the device to the skin.

Intravenous Injection

Sterile solutions can also be administered intravenously. The active ingredient may be prepared at a final dose of 1 ng to 10 g, preferably 1 mg to 1 g per Kg of body weight as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Preferred Uses of the Invention

The invention is applicable to both diagnostic, prevention and treatment purposes. A non-exclusive list of diagnostic uses is set forth in column 1 of Table 1 below. Columns 2–4 set forth, for each use, preferences regarding the manner in which certain diagnostic tests may be varied for best results.

TABLE 1

| Diagnostic test/Detection of Prostaglandin $D_2$ sythase | Preferred Population | Preferred Sample | Preferred Method of Detection |
|---|---|---|---|
| Renal Salt Wasting Syndrome | General, especially symptomatic patients | Urine or Plasma | ELISA |
| Alzheimer's Disease | Patients with dementia | Urine or Plasma | ELISA |

A non-exclusive list of treatment uses is set forth in column 1 of Table 2 below. Columns 2–4 set forth, for each use, preferences regarding the preferred pharmaceutical agent(s) to be used, the dosage and the manner of administration.

TABLE 2

| Treatment | Pharmaceutical Agent | Dosage | Administration |
|---|---|---|---|
| Renal Salt Wasting Syndrome | 1) Cyclo-oxygenase inhibitors such as indomethacin | 50 mg | Oral, three times daily |
|  | 2) Prostaglandin $D_2$ synthase monoclonal antibodies | 240 mg | Intravenous, once daily |
| Alzheimer's Disease | 1) Postaglandin $D_2$ synthase monoclonal antibodies. | 240 mg | Intravenous, once daily |

Experimental Details

Patient Selection. Patients were randomly recruited at the Division of Geriatric psychiatry, UMDNJ-Robert Wood Johnson Medical School based on their willingness to participate in the study. All subjects were examined by a board certified geriatric neuropsychiatrist who established the diagnosis of dementia. The bioassay was performed at Winthrop University Hospital. The protocol for these studies was approved by the respective institutional review boards of both institutions. Consent from demented patients was obtained from their legal guardian on all cases. Seventeen subjects with Alzheimer's disease met NINCDS-ADRDA criteria for probable Alzheimer's disease (G. McKhann et al., Neurol. 34:939–944, 1984) and 11 multi-infarct dementia (MID) subjects met DSM-IIIR criteria for the diagnosis of MID and had Hachinski Ichemia Scale scores greater than 7 (American Psychiatric Association. Diagnostic and Statistical manual of mental disorder. 4th edition (1994). Am. Psychiatric Assoc. Washington, D.C. Dementia Work Group: Gary J. Tucker, Chairperson; V. C. Hachinski et al., Arch. Neurol. 32:632–637, 1975). Nine subjects of the same age and gender distribution served as normal controls (C). In addition to the routine testing, all patients received either a CT scan or magnetic resonance imaging of brain and Mini-Mental State Examination (MMSE) score (M. F. Folstein et al., J. Psychiatric Res. 12:189–198, 1975). Heparinized whole blood from all subjects was centrifuged at 1500 g for 10 minutes at 4° C. within 30 min. after collection; the plasma was then transferred to a new plastic tube and stored at −70° C. all samples were stored at −70° C. until time of bioassay, except during overnight shipping on dry ice.

Cell Culture and Assay Protocol. LLC-PK1, a pig kidney epithelial cell line was plated at a density of $10^3$ cells per well into eight-well Permanox plastic chamber slides (NUNC, Naperville, Ill.). The cells were cultured at 37° C. in 5% $CO_2$ in humidified incubators and grown for 3 days to 70–80% confluency in DMEM-F12 that was supplemented with 10% fetal calf serum, 7.5% sodium bicarbonate, 15 mM HEPES, 200 mM L-Glutamate, 100 u penicillin and 0.1 ug/ml streptomycin (Life Technologies, Gaithersburg, Md.). The culture fluid was then removed and cells were exposed to plasma from control individuals, Alzheimer's disease patients or multi-infarct dementia patients diluted 1:5 in fresh DMEM-F12 media, supplemented as above, for 2 h at 37° C. The cells were then rinsed in PBS, and fixed in 4% formaldehyde in PBS for 10 min., permeabilized with 0.5% Triton X-100 (Sigma Chemical CO., St. Louis, Mo.) for 5 min. and washed in 4 changes of distilled water. A positive control was obtained by exposing cells to 0.6 mM $H_2O_2$ diluted in DMEM-F12 for 2 h.

Apoptosis Assay (TUNEL): Nuclear DNA fragmentation consistent with apoptosis was determined by the method of TdT-mediated dUTP-biotin nick-end labeling (TUNEL) (Y. Gavrieli et al., J. Cell. Biol. 119:493–501, 1992). The ApopDetek cell death assay kit (Enzo, Farmingdale, N.Y.) was used utilizing terminal deoxynucleotide transferase to incorporate Bio-16-dUTP onto the 3'-OH termini in the DNA of apoptotic cells, subsequent binding with streptavidin-horseradish peroxidase, and visualization after conversion of the substrate and chromagen (hydrogen peroxide and aminoethylcarbazole) into a localized brick red precipitate. A blue counter stain was also used. Slides were then observed for morphologically irregular and condensed nuclei which contain dark red precipitate to indicate TUNEL-positive cells using a Nikon (Nikon, Inc., Melville, N.Y.) Optiphot microscope. Five to six random field totaling approximately 1,000 to 1,500 cells were counted per slide. Apoptotic index (AI), defined as the percent of cells undergoing apoptosis, is calculated by dividing the number of positive nuclei by the total number of nuclei counted multiplied by 100.

Dose and Time-Response Studies. The TUNEL assay was performed in LLC-PK1 cells that were exposed to different dilutions of plasma of patients with Alzheimer's disease and control plasma at different intervals of time. Alzheimer's disease and control plasma were diluted with DMEM-F12 at 1:100, 1:20, 1:10; 1:5, 1:3 and 1:2 and added to 70–80% confluent LLC-PK1 cells for 2 h; conversely, Alzheimer's disease and control plasma were diluted 1:5 with DMEM-F12 and exposed to LLC-PK1 cells for 60, 90, 120 and 180 min. The selection of 2 h exposure in the dilution studies and 1:5 dilution of plasma in the time response studies were based on maximum apoptotic index noted with the respective studies.

Electron Microscopy. LLC-PK1 cells were plated at $10^3$ cells per 35 mm plastic petri dish, exposed to Alzheimer's disease or control plasma at 1:5 dilution in DMEM-F12 for 2 h and fixed with 2.5% glutaraldehyde in 0.1M sodium cacodylate, pH 7.2, for 1 h at 4° C. The cells were then postfixed in 1% buffered osmium tetroxide, dehydrated in a graded series of ethanol, and embedded in LX112 (Ladd Research Industries, Burlington, Vt.). En fac and cross-sectional thin sections were stained with uranyl acetate and lead citrate and examined on a Zeiss EM10 transmission electron microscope.

DNA Ladder Assay. DNA ladder was observed using a modification of the procedure described by Eastman (Eastman, A. "Assays for Features Associated with Apoptosis" in Meth. Cell Biol. 46:41–55 edited by L. M. Schwartz and B. A. Osborne, Academic Press). LLC-PK1 cells (10$^6$) were seeded into T75 flasks (Falcon) containing 10 ml of DMEM-F12—10% fetal calf serum supplemented with 0.12% NaHCO$_3$, 5 mM glutamine, 15 mM HEPES and 1% pen/strep. Cells were allowed to attach overnigh at 37° C. in 5% humidified CO$_2$. Five ml of medium were withdrawn and 0.5 ml of test plasma added. Cells in the medium and adherent cells (0.05% trypsin in 0.53 mM EDTA, GIBCO, 3 min., 37° C.) were harvestedon days 2, 3, 4, and 5 by centrifugation at 142×g for 3 min. at room temperature. The cellpellet was warmed to 50° C. for 2–3 min. and resuspended in 2% Sea Plaque agarose (FMC, Rockland, Me.) in 0.125 M EDTA pH 7.4, and dispensed into a precooled (4° C.) mold. The agarose plugs were incubated at 50° C. for 2 h in 0.5 M EDTA pH 8.0, 1% sarcosine (Sigma), and 1 mg/ml of proteinase K (Boehringer Mannheim). Plugs were then incubated at 37° C. for 30 min. in 10× volume of 10 mM TrisHCl pH 7.5, 50 mM EDTA. The buffer was exchanged with TE (10 mM TrisHCl pH 7.5, 1 mM EDTA), RNase A, previously boiled for 15 min (Sambrook, J., E. F. Fritsch, and T. Maniatis, "Molecular Cloning: A Laboratory Manual", Cold Spring Harbor, N.Y., Cold Spring Harbor Laboratory Press, 1989), was added to a final concentration of 250 μg/ml, and the plugs incubated an additional 50 min. at 37° C. DNA in the plugs was subjected to electrophoresis through a 2% SeaKem (FMC) agarose gel in TAE buffer (Sambrook, J., E. F. Fritsch, and T. Maniatis, "Molecular Cloning: A Laboratory Manual", Cold Spring Harbor, N.Y., Cold Spring Harbor Laboratory Press, 1989) at 2V/cm for 14 h and visualized as described (Eastman, A. "Assays for Features Associated with Apoptosis" in Meth. Cell Bio. 46:41–55 edited by L. M. Schwartz and B. A. Osborne, Academic Press).

Partial Protein Purification and Heating of Plasma. Pooled plasma from Alzheimer's disease and control subjects were dialyzed in a 10 kDa m.w. cut-off membrane in 20 mM phosphate buffer, pH 7.1, and centrifuged at 13,000 g for 15 min. The clear supernatant was loaded into 10 ml of an Affi-Gel Blue Gel affinity column (Bio-Rad Laboratories, Hercules, Calif.). The column was then washed with loading buffer until protein levels were not detectable, followed by the sequential elution with 0.5 M and 2 M NaCl in buffer. Protein concentration was monitored by UV absorbance at 280 nm. The three protein fractions (load and wash, 0.5 M NaCl and 2 M NaCl) were dialyzed in a 10 kDa m.w. cut-off membrane, concentrated over a bed of PEG 8000 in a 1 kDa m.w. cut-off membrane and dialyzed in a 10 kDa m.w. cut-off membrane against 10 mM phosphate buffer, pH 7.1. Cultured LLC-PK1 cells were then exposed to 30–100 ug of the two pooled fractions for 2 h at 37° C. and a TUNEL assay performed.

In separate experiments, Alzheimer's disease and control plasma were heat-treated at 56° C. for 30 min. In some experiments, plasma was boiled at 100° C. for 5 min. and the denatured protein aggregates removed by sedimentation at 1,000 g for 1 min. prior to testing by TUNEL assay as noted above. In separate experiments, Alzheimer's disease plasma was alternately frozen at −70° C. and thawed to room temperature at least 3 times and a TUNEL assay performed in LLC-PK1 cells after a 2 h exposure to a 1:5 dilution of the plasma with DMEM-F12 at 37° C.

Isoelectric Focusing. The active fraction from the Affi-Gel Blue-Gel run (0.5 M NaCl) was further fractionated by isoelectric focusing (IEF) using Fotofor (Bio-Rad). This active fraction was run at a pH gradient of 3–10, using Bio-Lyte ampholyte 3/10, at a constant power of 15 W at 4° C. for 4 h. Fractions were pooled according to their protein profile and assayed for apoptotic activity. Fractions with highest apoptotic index were pooled, dialyzed and refractionated by IEF using a narrow pH gradient of 4–6, at the same settings, utilizing Bio-Lyte ampholyte 4/6 and 3/10, 80:20%, respectively (Bio-Rad Laboratories, Hercules, Calif.).

Effect of Protein Synthesis on Apoptotic Activity. LLC-PK1 cells were exposed to Alzheimer's disease and control plasma in the absence and presence of cycloheximide (0.2–200 uM) (Sigma, St. Louis, Mo.). Apoptotic index was measured in these cells by TUNEL assay.

Effect of Calcium Depletion on Factor Activity. The TUNEL assay was performed in the usual manner except for substituting DMEM-F12 with calcium-free DMEM, supplemented with dialyzed 10% fetal calf serum (Life Technologies, Grand Island, N.Y.) and 0.6 mM EGTA to chelate calcium. Dialyzed Alzheimer's disease and control plasma were then added to the calcium-free media for 2 h at 37° C. and a TUNEL assay performed.

Contribution of Known Apoptotic Inducers. To test the possibility that the apoptotic factor in Alzheimer's disease plasma was β amyloid, TNF-α or myeloma light chain, the TUNEL assay was repeated as above after a 2 h incubation at 37° C. with 0.10–50 mM β amyloid (Peninsula Laboratories, Inc., Belmont, Calif.), 5 pM-3 nM TNF-α (Quantikine, Minneapolis, Minn.) and 3–60 ug λ myeloma light chain, kindly supplied by Dr. Vecihi Batuman, Tulane University School of Medicine, New Orleans, La. To eliminate the possibility that a protease in Alzheimer's disease plasma is responsible for the apoptotic activity, the effect of a broad spectrum protease inhibitor cocktail (Boehringer Mannheim) was studied on apoptotic index using the TUNEL assay. LCC-PK1 cells were incubated with Alzheimer's disease plasma with and without the inhibitor cocktail and assayed as detailed above. This cocktail inhibits a large spectrum of serine, cysteine, and metalloproteases as well as calpains. It consists of aprotinin, leupeptin, EDTA, and pefabloc.

Statistical Analysis. All TUNEL assays were performed in triplicate and the data expressed as the mean±SEM. An unpaired Student's T test was used to compare one set of experiments from the other and a $P<0.05$ was deemed significant. A multivariate analysis was used to determine whether any medications taken by the patients might affect the results or if there was a correlation between apoptotic index and MMSE score.

EXAMPLE 1

Figure 2:
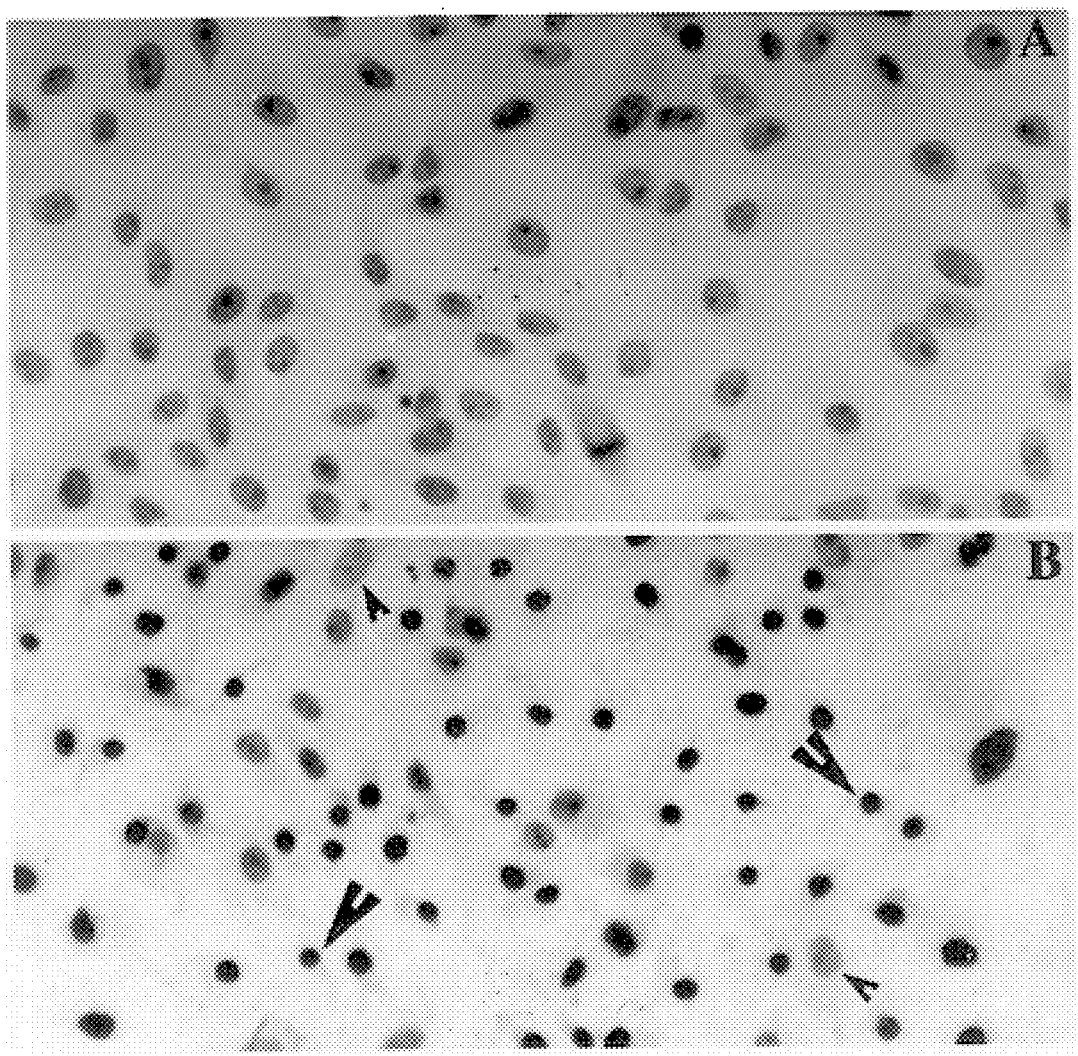
FIGS. 2A and 2B illustrate a TUNEL assay with ApoDetek Kit (Enzo).

A Factor in the Plasma of Patients with Alzheimer's Disease Causes Apoptosis; Partial Purification and Characterization of the Factor Electron microscopy of LLC-PK1 cells after incubation with Alzheimer's disease plasma (see Experimental Details) illustrates the distinct pattern of apoptotic cells. Apoptotic cells have condensed, black nuclei and some cells are noted to be shrunken and engulfed by neighboring cells, FIG. 1. Light microscopic view of these cells that had been labeled in situ by TUNEL method are depicted in FIG. 2.

Figure 3A:
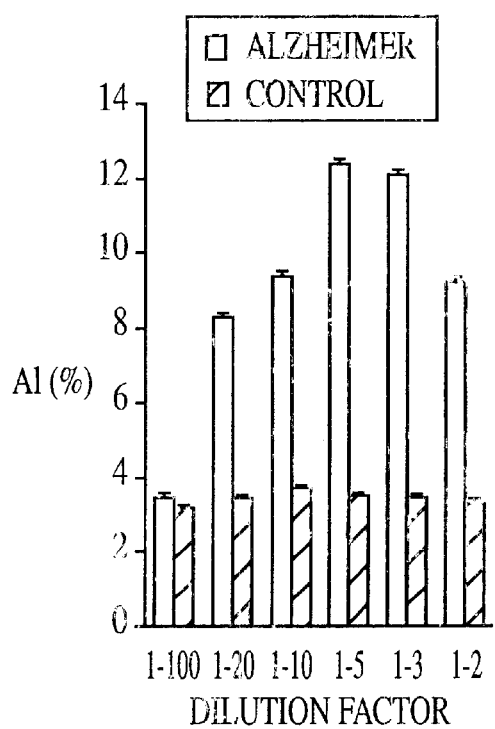
FIGS. 3A and 3B show a dose response (A) and Time course (B) of apoptosis in LLC-PK1 cells exposed to plasma of patients with Alzheimer's disease as measured by TUNEL assay. This shows that AD plasma contains a component that causes LLC-PK1 cells to undergo apoptosis.
Figure 3B:
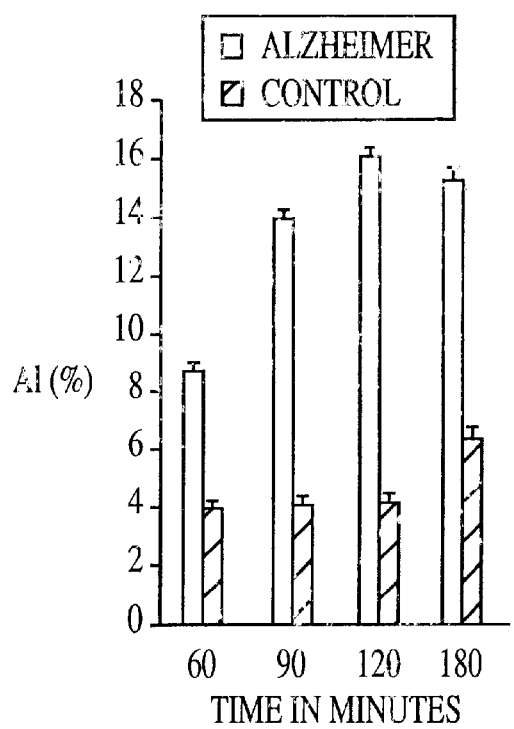

Table 3 summarizes the results of the exposure of LLC-PK1 cells to plasma from control individuals, patients with Alzheimer's disease and multiple infarct dementia. There was a nearly fourfold increase in apoptotic index in LLC-PK1 cells that were exposed to Alzheimer's disease plasma (25.6±8.8%) as compared to control plasma (6.0±2.4%), P<0.001, and multiple infarct dementia plasma (6.5±2.3%), p<0.001. There was no significant difference in apoptotic index between control plasma and multiple infarct dementia plasma, p>0.05. As noted in FIG. 3B, apoptotic index increased progressively as the time of incubation with Alzheimer's disease plasma increased, peaking at 2 h with an apoptotic index of 16.1±0.3%. Diluting Alzheimer's disease plasma in a range of 1:2 to 1:100 revealed a maximum apoptotic index of 12.4±0.2% at 1:5 dilution of plasma with medium (FIG. 3A). There was no correlation between apoptotic index and the medications the patients had been taking at the time of study or the MMSE scores in Alzheimer's disease.

TABLE 3

Apoptotic index in LLC-PK1 cells exposed to control, Multi-Infarct dementia, and Alzheimer's disease patient's plasma

|  | AI (%) |
| --- | --- |
| Alzheimer's Plasma | 25.6 ± 8.8 |
| MID Plasma | 6.5 ± 2.3 |
| Control Plasma | 6.0 ± 2.4 |

Figure 4:
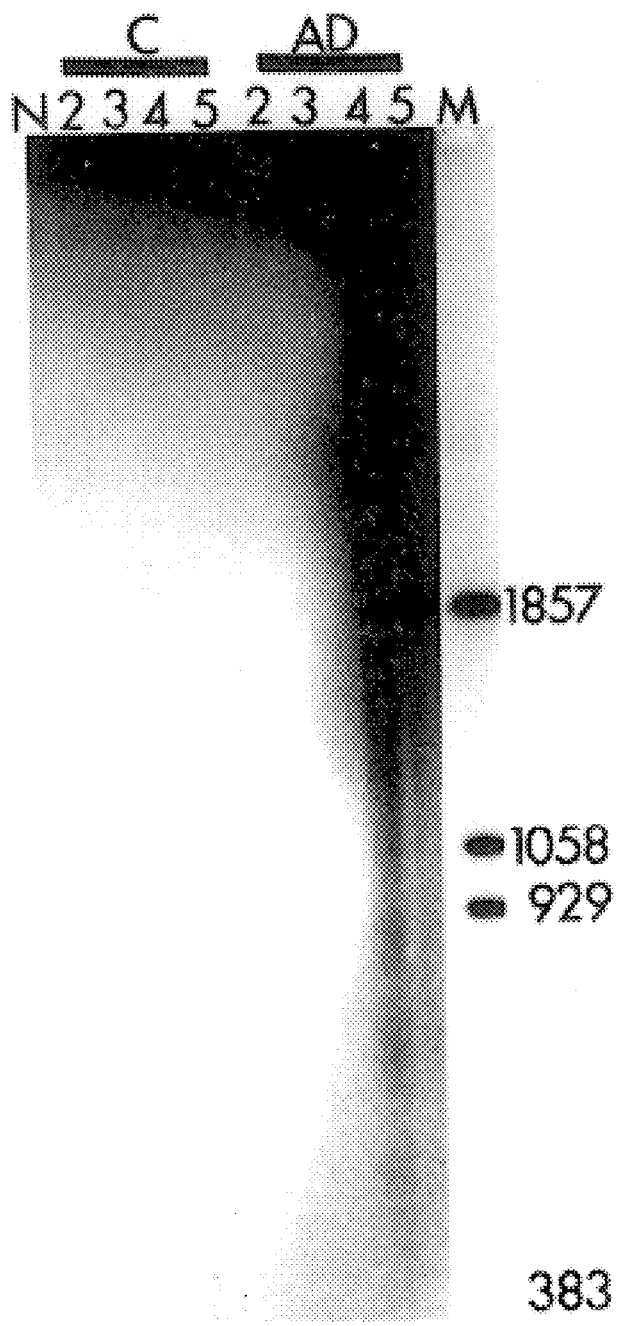
FIG. 4 shows internucleosomal DNA cleavage in LLC-PK1 cells that had been exposed to plasma of patients with Alzheimer's disease (AD) for intervals 2, 3, 4, and 5 days. Maximum DNA fragmentation was 4 days after exposure to AD plasma and showed the characteristic 180 bp spacing. Control (NC) plasma did not exhibit a ladder even after incubation for 5 days. The DNA laddering indicates that apoptosis occurs in LLC-PK1 cells exposed to AD plasma.

FIG. 4 shows internucleosomal DNA cleavage in LLC-PK1 cells that had been exposed to plasma from patients with Alzheimer's disease (AD) for intervals of 2, 3, 4, and 5 days. Maximum DNA fragmentation was 4 days after exposure to AD plasma and showed the characteristic 180 bp spacing. Control (NC) plasma did not exhibit a ladder even after incubation for 5 days.

As noted in Table 4, elimination of calcium from the incubating medium, fetal bovine serum and plasma or incubation with 200 uM cycloheximide resulted in inhibition of apoptosis by Alzheimer's disease plasma, suggesting that apoptosis in the system is dependent on the level of extracellular calcium and protein synthesis. There was no inhibition of apoptosis at the lower concentrations of cycloheximide. In a separate group of experiments, heating Alzheimer's disease and control plasma at 56° C. for 30 min., which deactivated complement, did not alter the apoptotic activity, table 4. However, boiling the Alzheimer's disease plasma at 100° C. for 5 min. resulted in AI that was not different from control plasma. Moreover, freezing and thawing the plasma from −70° C. to room temperature at least three times decreased apoptotic activity, table 4. These data suggest that the apoptotic factor in Alzheimer's disease plasma is a protein.

TABLE 4

Characteristics of Apoptotic Factor

| Plasma | Alzheimer's Plasma AI (%) | Control AI (%) |
| --- | --- | --- |
| No treatment | 25.6 ± 8.8 | 6.0 ± 2.4 |
| 56° C., 30 min. | 19.5 ± 2.7 | 8.3 ± 2.5 |
| 100° C., 5 min. | 4.7 ± 2.2 | 8.7 ± 1.2 |
| Cycloheximide |  |  |
| (200 uM) | 7.7 ± 1.6 | 6.3 ± 1.5 |
| (0.2–20 uM) | 28.7 ± 4.0 | 5.0 ± 0.0 |
| Ca$^{++}$ free medium | 6.3 ± 1.6 | 4.0 ± 0.7 |
| Freeze and thaw | 6.0 ± 2.4 | 5.3 ± 1.5 |

To exclude the possibility that the factor is β-amyloid, cells were incubated with 0.1, 10 and 50 uM of β-amyloid dissolved in media. No detectable apoptotic activity was observed even at 50 uM, AI=6.1±3.1%. To eliminate the possibility that TNF-α might be the apoptotic factor, control and Alzheimer's disease plasma were quantified for the presence of TNF-α by ELISA (Quantikine). The levels of TNF-α in control and Alzheimer's disease plasma were less than the lowest level of detection by the ELISA kit of 0.3 pM. We achieved a standard curve with the ELISA with TNF-α standards and blocked the reaction, utilizing TNF-α antibody. We also tested the effect of TNF-α on LLC-PK1 cells at 5, 50, 500, and 3000 pM for 2 h and found that doses as high as 50 pM yielded background levels of apoptosis, AI=6%. On a Western blot both the control and Alzheimer's disease plasma resulted in no signal, while a positive control of 100 ng TNF-α yielded a positive signal. A similar situation occurred with interleukin-1β. Both control and Alzheimer's disease plasma had undetectable levels of interleukin 1β by ELISA.

Figure 5:
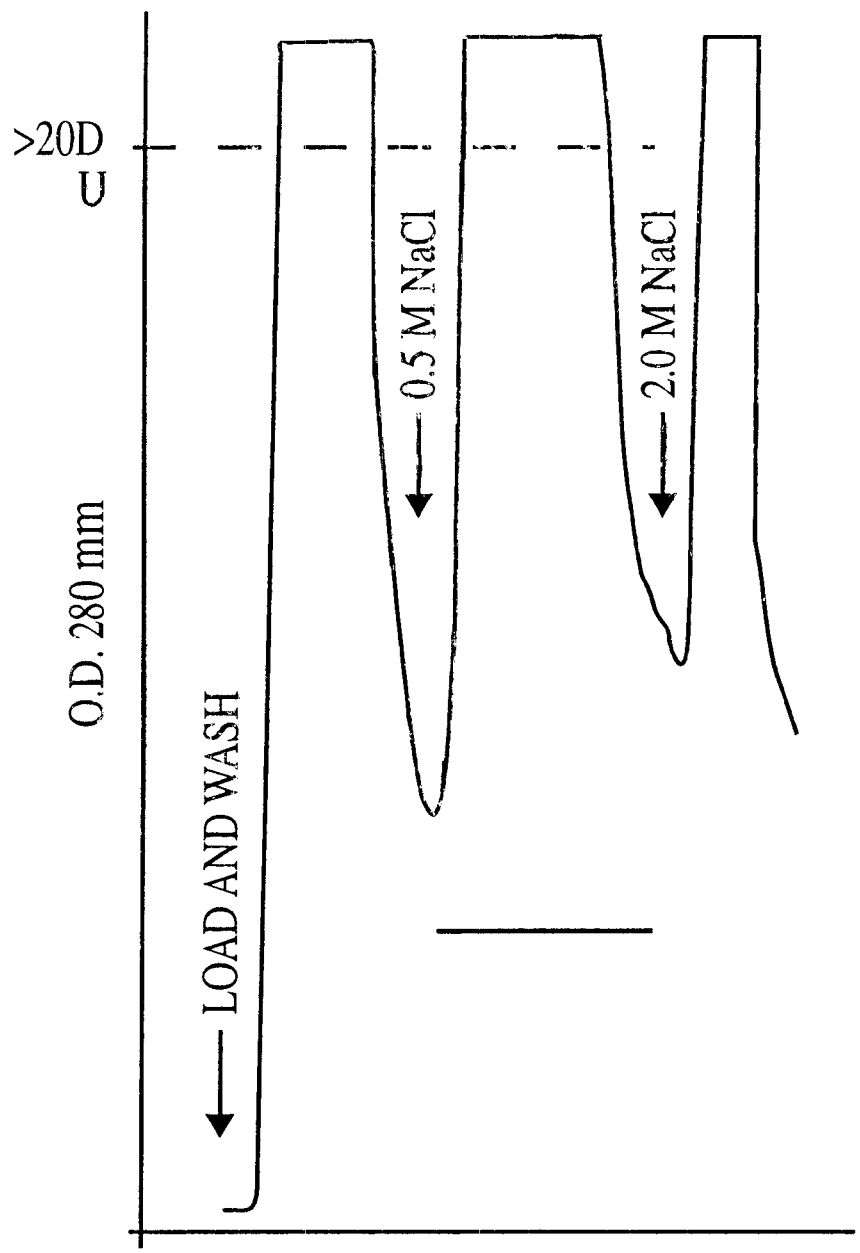
FIG. 5 is an elution profile of pooled plasma from patients with Alzheimer's disease (4.5 mL) chromatography on (1×8 cm) Affi-Gel Blue Gel Agarose column (20 mM phosphate Buffer, pH 7.1) (Flow Rate=1 mL/min.) (15 mL Load and Wash, 25 mL 0.5 M NaCl fraction, 10 mL 2M NaCl fraction). Line represents active fraction.
Figure 6A:
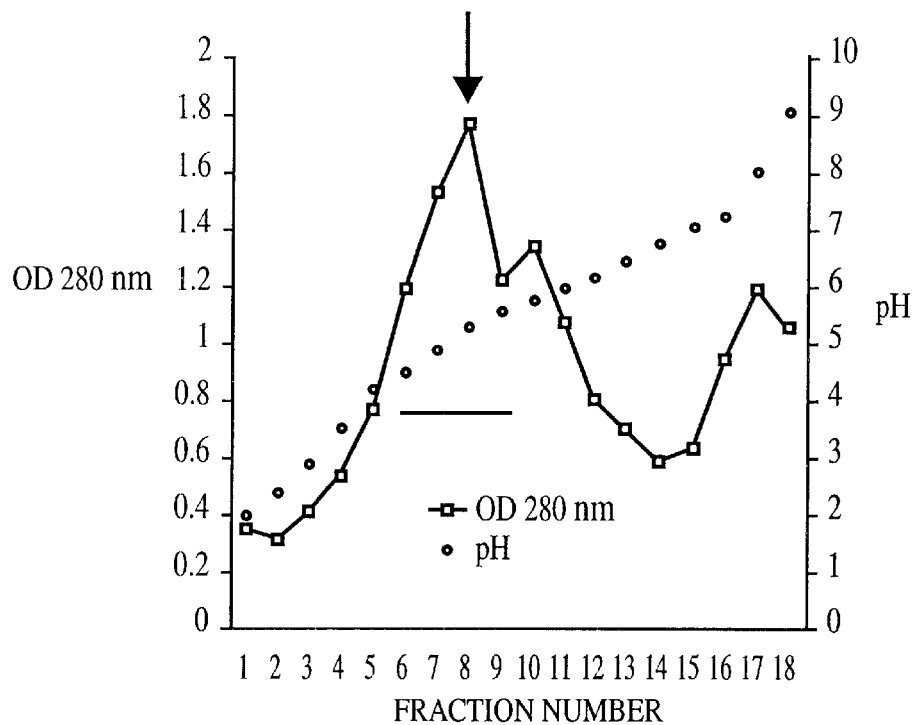
FIGS. 6A and 6B show the results of iso-electric focusing.
Figure 6B:
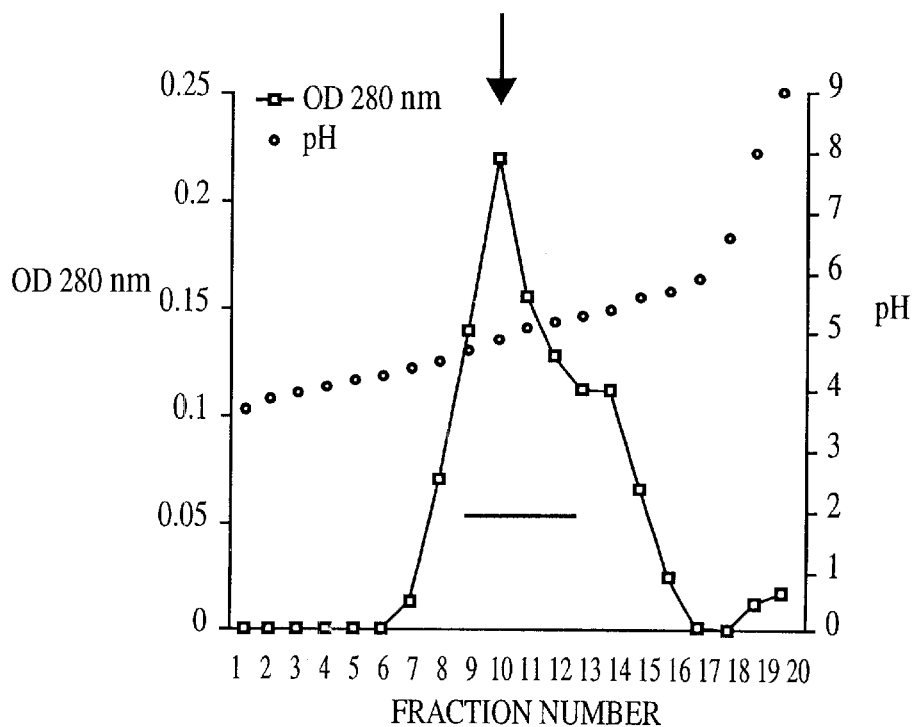

FIG. 5 depicts the protein profile from each individual step of purification on a Affi-Gel-Blue-Gel column. The highest AI of 21% was found in the 0.5 M NaCl eluate. No activity was found in the load and wash fraction and only a modest activity was noted in the 2M NaCl eluate, AI of 6% vs. 9%, respectively. The 2M NaCl eluate was mainly composed of albumin. The active fraction (0.5 M NaCl eluate) was dialyzed overnight in a 10 kDa m.w. cut-off membrane at 4° C. against 10 mM phosphate buffer, pH 7.1 to remove salt. Isoelectric focusing was performed on this protein fraction at a pH gradient of 3–10, FIG. 6A. Fractions within clearly defined protein peaks were pooled and dialyzed to remove ampholyte, followed by a TUNEL assay to monitor for apoptotic activity. Dialysis with a 10 kDa m.w. cut-off membrane demonstrated retention of apoptotic activity in the dialysis bag, suggesting that the size of the protein exceeded 10 kDa. The highest AI of 29.4% was noted in fraction 2 of the pooled samples and isoelectric focusing repeated only on this active fraction at a narrow range pH gradient of 4–6, FIG. 6B. The active fraction with an AI of 22% was noted in fraction 2 of this additional purification step. The pI range of both fractions was 4.7–5.5.

EXAMPLE 2

Isolation and Identification of Prostaglandin D$_2$ Synthase

Eleven liters of urine were collected from a patient suffering from renal salt wasting syndrome. The protein was precipitated from the urine with 80% ammonium sulfate and centrifuged to get a pellet. A portion of the pellet was dissolved in 25 mM Tris.HCl at pH 7.5 and then dialyzed overnight in the same buffer in a 10 kDa cutoff membrane. The dialyzed proteins were then loaded onto a High-Trap Q Sepharose column. The proteins were eluted off this column with 0.5M NaCl and 1.0 M NaCl in several fractions. These fractions were then dialyzed in a phosphate buffer at pH 7.1. Subsequently the fractions were assayed for their ability to induce apoptosis (see Experimental Details) and the activity was found in the 0.5M NaCl. Following this, isoelectric focusing (see Experimental Details) was performed from pH 3 to 10 and fractions were collected. The active fraction (pH 4.8–5.5) was further purified by HPLC-C$_{18}$ column. The active fraction from this column was found in a single peak. The active fraction was placed on SDS PAGE gel and proteins with molecular weight of 29, 32, 33, and 42 Kd were eluted from the gel and assayed for activity. The activity was found to be associated with the 32 Kd band.

Following the above procedure, the 32 Kd band was sequenced and found to contain 2 proteins, one of which is $\alpha_1$ microglobulin. Since $\alpha_1$ microglobulin was found to have no apoptotic activity, it was absorbed on a protein A column to which the $\alpha_1$ microglobulin-specific antibody was attached. The result was a pure 23–29 $kD_2$ band protein as seen on an SDS PAGE gel. The single 23–29 $kD_2$ protein was transferred from SDS-PAGE gel to a protein sequencing membrane and sequenced. With two separate analyses based on the first 20 N terminal amino acids, the apoptotic factor was positively identified as prostaglandin $D_2$ synthase which sequence was described by Nagata et al. (Proc. Natl. Acad. Sci. USA, 88:4020–4024; 1991).

EXAMPLE 3

Modulation of the Synthesis of $-\Delta^{12}$Prostaglandin $J_2$

Prostaglandin $D_2$ synthase is an enzyme involved in the $-\Delta^{12}$Prostaglandin $J_2$ synthesis pathway. The following is an illustration of this pathway.

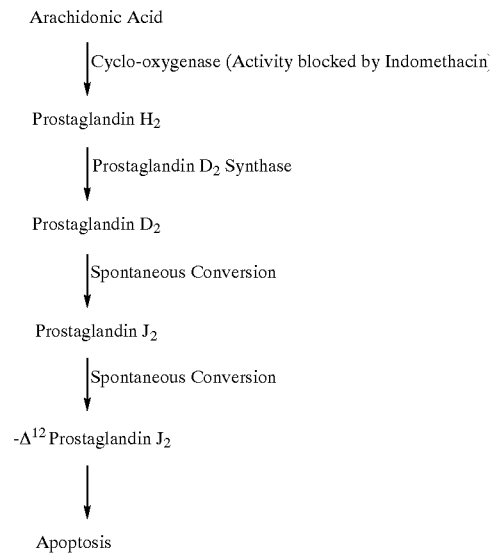

Prostaglandin $D_2$ Synthase increased apoptosis of human kidney proximal tubule cells in culture about four times above control (see Experimental Details). To find out which prostaglandin is responsible for inducing apoptosis, the different prostaglandins were tested for their ability to induce apoptosis in kidney proximal tubule cells. $-\Delta^{12}$Prostaglandin $J_2$ was found to be the only prostaglandin listed above that induces apoptosis. It induced apoptosis to the same degree as Prostaglandin $D_2$ Synthase. Also, Prostaglandins E, H and D did not increase apoptosis.

Adding Indomethacin, which blocks cyclo-oxygenase reduces the prostaglandins downstream and inhibited apoptosis to baseline. Furthermore, the simultaneous addition of Indomethacin and Prostaglandin $D_2$ Synthase did not increase apoptosis above baseline. In addition, the deactivation of Prostaglandin $D_2$ Synthase by N-Ethyl Maleimide inhibited apoptosis. The combination of Indomethacin, Prostaglandin $D_2$ Synthase and $-\Delta^{12}$Prostaglandin $J_2$ increased apoptosis and so did the addition of $\Delta^{12}$Prostaglandin $J_2$ to Indomethacin increased apoptosis.

In combination, these results indicate that prostaglandin $D_2$ synthase increases apoptosis by increasing the production of prostaglandin $D_2$ which necessarily results in the production of $-\Delta^{12}$Prostaglandin $J_2$. It is therefore the activity of $-\Delta^{12}$prostaglandin $J_2$ that clinical techniques should seek to reduce. Indirect methods such as reducing activity of prostaglandin $D_2$ synthase or reducing any "upsteam" synthesis of $-^{12}$prostaglandin $J_2$, or a precursor thereto, is quite useful. Increased catabolism of $-\Delta^{12}$prostaglandin $J_2$, its upstream precursors, or enzymes involved in its synthesis is also expected to be effective. Naturally, direct inhibition of $-\Delta^{12}$prostaglandin $J_2$ activity (e.g. using a $-\Delta^{12}$prostaglandin inhibitor, e.g. a receptor antagonist) may also provide therapeutic effect.

EXAMPLE 4

Production of Antibodies to Prostaglandin $D_2$ Synthase

EST's homologous to mRNA for the glutathione independent PGD2S were obtained from ATCC and assembled into a full-length cDNA and a premature stop codon mutation corrected. The full-length cDNA was inserted into a bacterial expression vector, pMAL-C2, joining the vector encoded carrier protein to the PGD2S coding sequence at the signal peptidase cleavage site. Purified recombinant fusion protein was purified by affinity chromatography, cleaved with factor Xa, and the carrier protein separated from the recombinant factor by ion exchange chromatography. One milligram of purified recombinant factor was mixed with Titermax adjuvant and injected intradermally in a New Zealand white rabbit. Five weeks later, the rabbit was boosted with another milligram of recombinant factor in adjuvant and serum collected 10 days later. Polyclonal antisera from this rabbit was able to detect 1 nanogram of reduced recombinant factor in a Western blot. This antisera also reacted in a Western blot with PGD2S from a natural source and which had the same MW as described in the literature.

Although the present invention has been described in relation to particular embodiments thereof, many other variations and modifications and other uses will become apparent to those skilled in the art. The present invention therefore is not limited by the specific disclosure herein, but only by the appended claims.

What is claimed is:

1. A method of assessing the likelihood that a patient is afflicted with Alzheimer's disease, said method comprising measuring the level of prostaglandin $D_2$ synthase in a urine sample from said patient and comparing said level to a normal level of prostaglandin $D_2$ synthase in urine samples taken from normal non-demented age and gender-matched control individuals, wherein a prostaglandin $D_2$ synthase level of at least twice the level found in the normal individuals is an indication that the patient is likely afflicted with Alzheimer's disease.

2. The method of claim 1, wherein prostaglandin $D_2$ synthase is measured by contacting said sample with antibodies to prostaglandin $D_2$ synthase, and determining levels of immunocomplexes between said antibodies and said prostaglandin $D_2$ synthase.

3. The method of claim 1, wherein prostaglandin $D_2$ synthase is measured by western blotting or immunoprecipitation.

* * * * *